(12) United States Patent
Fukatsu et al.

(10) Patent No.: US 8,183,404 B2
(45) Date of Patent: May 22, 2012

(54) PROCESS FOR PRODUCING DICYANONORBORNANE AND ZEROVALENT NICKEL COMPLEX CATALYST

(75) Inventors: Norihiko Fukatsu, Omuta (JP); Hiroyuki Morijiri, Yokohama (JP); Chitoshi Shimakawa, Arao (JP); Koichi Tokunaga, Chikugo (JP); Seiichi Kobayashi, Omuta (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 568 days.

(21) Appl. No.: 12/306,889

(22) PCT Filed: Jun. 22, 2007

(86) PCT No.: PCT/JP2007/000680
§ 371 (c)(1),
(2), (4) Date: Jan. 9, 2009

(87) PCT Pub. No.: WO2008/001490
PCT Pub. Date: Jan. 3, 2008

(65) Prior Publication Data
US 2009/0198082 A1    Aug. 6, 2009

(30) Foreign Application Priority Data
Jun. 30, 2006  (JP) ................. 2006-181025

(51) Int. Cl.
*C07C 253/10*    (2006.01)
(52) U.S. Cl. ..................................... 558/348
(58) Field of Classification Search .......... None
See application file for complete search history.

(56) References Cited

U.S. PATENT DOCUMENTS

| | | |
|---|---|---|
| 2,666,780 A | 1/1954 | Arthur, Jr. et al. |
| 3,328,443 A | 6/1967 | Clark et al. |
| 5,087,722 A | 2/1992 | Inomata et al. |

FOREIGN PATENT DOCUMENTS

| | | |
|---|---|---|
| JP | 3-95151 A | 4/1991 |
| JP | 03-232850 A | 10/1991 |
| JP | 6-184082 A | 7/1994 |
| JP | 2002-69043 A | 3/2002 |
| JP | 2003-55328 A | 2/2003 |

OTHER PUBLICATIONS

Hedoux, et al., Physical Review B, 58:31 at 31 (1998).*
Jacques, et al., Macromolecules 29:3129 at 3129 (1996).*
'12996 no Kagaku Shohin', The Chemical Daily Co., Ltd., Jan. 24, 1996, p. 992, ISBN 4-87326-204-6 C3543.
Edited by Tokyo Kasei Kogyo Co., Ltd. Gakujutsubu, 'Sogo Catalog No. 34' {1998 NenBan), Tokyo Kasei Hanbai Kabushiki Kaisha, p. 1500.
Meruku Kabushiki Kaisha Shiyaku Life Science Jigyobu, 'Meruku Shiyaku Catalog', first edition, Apr. 1, 2002, 'Triphenyl Phosphite'.
International Search Report (PCT/ISA/210), Jan. 6, 2009.
Veronesi et al., "Biochemical and Neuropathological Assessment of Triphenyl Phosphite in Rats," Toxicology and Applied Pharmacology, 1986 vol. 83, pp. 203-210.
Office Action from Chinese Patent Office issued in corresponding Chinese Patent Application No. 200780017428.5 dated Aug. 5, 2011.

* cited by examiner

*Primary Examiner* — Yong Chu
*Assistant Examiner* — Michael Barker
(74) *Attorney, Agent, or Firm* — Buchanan Ingersoll & Rooney PC

(57) ABSTRACT

The present invention is to provide a process for producing dicyanonorbornane characterized by causing hydrogen cyanide to undergo addition reaction with cyanonorbornene (bicyclo[2.2.1]-5-heptene-2-carbonitrile) in the presence of a zerovalent nickel complex catalyst which is produced by using a phosphite represented by P(x)(y)(z) (wherein P is a phosphorus atom, and x, y and z are each OR, where R represents an aryl group having not more than 18 carbon atoms) as a ligand to reduce a nickel halide with at least one metal selected among zinc, cadmium, beryllium, aluminum, iron and cobalt, wherein the phosphite is one which has a phosphate content of 1.0 weight % or lower based on the whole phosphite.

4 Claims, No Drawings

US 8,183,404 B2

PROCESS FOR PRODUCING DICYANONORBORNANE AND ZEROVALENT NICKEL COMPLEX CATALYST

TECHNICAL FIELD

The present invention relates to a process for producing dicyanonorbornane. Further, the invention relates to a zerovalent nickel complex catalyst.

BACKGROUND ART

In the past, as a process for producing dicyanonorbornane (hereinafter referred to as DCN) by causing hydrogen cyanide to reaction with cyanonorbornene (hereinafter referred to as CNN), for example, the following methods are known:

1) a method involving using a cobalt carbonyl catalyst and triphenyl phosphine as a catalyst system (refer to Patent Document 1); and 2) a method involving using a zerovalent nickel complex catalyst and a Lewis acid as a catalyst system (refer to Patent Documents 2 and 3).

However, in the above methods 1) and 2), since the yield was low, an expensive catalyst was used and the methods were for isolating a complex involving a purification step, there have been problems in the decreased yield and the troublesome workability.

Then, there has been proposed a new method regarding the synthesis of a zerovalent nickel complex catalyst or the like, enabling to overcome conventional problems in such techniques (refer to Patent Document 4). According to the method as described in Patent Document 4, the synthesis of the zerovalent nickel complex catalyst was extremely easy and the yield became high.

However, it has been known that 2,5(6)-bis aminomethyl-bicyclo[2,2,1]heptane (hereinafter referred to as NBDA) obtained by the catalytic hydrogenation of DCN obtained by using the method as described in Patent Document 4 as a raw material has a property that time-dependent coloring is extremely great. It has been known that phenol remained in a raw material DCN is also mixed in NBDA as an impurity, whereby time-dependent coloring occurs. That is, this coloring is mainly caused by phenol contained in NBDA. Accordingly, in order to reduce coloring, there has been proposed a method involving prescribing the amount of phenol in NBDA for reducing the amount of phenol in the purification step (refer to Patent Document 5).

Patent Document 1: U.S. Pat. No. 2,666,780
Patent Document 2: Japanese Patent Laid-open No. 1991-95151
Patent Document 3: U.S. Pat. No. 3,328,443
Patent Document 4: Japanese Patent Laid-open No. 2003-55328
Patent Document 5: Japanese Patent Laid-open No. 2002-69043

DISCLOSURE OF THE INVENTION

When the method of Patent Document 5 was used, it was possible to avoid time-dependent coloring of NBDA. However, there was a variation in the amount of phenol due to a raw material of a zerovalent nickel complex catalyst which is used for causing hydrogen cyanide to undergo addition reaction with CNN. Namely, the amount of phenol generated when NBDA is obtained by the catalytic hydrogenation of the obtained DCN is varied depending on the difference in the production maker or production lot of a phosphite used as a raw material and handling status right before the use. Accordingly, an operation of adjusting caustic soda or the like is troublesome in association with the amount of phenol in DCN when NBDA is distilled by adding caustic soda, and in addition, the phenol is present in the obtained NBDA even though the phenol in DCN is removed in advance, causing time-dependent coloring in some cases.

In order to solve the above objects, the present inventors have conducted an extensive study and as a result, have found the following matters. That is, it was confirmed that a phosphate present as an impurity in a phosphite as a ligand of a complex catalyst used when DCN is produced by causing hydrogen cyanide to reaction with CNN is also present in DCN as an impurity, and phenol is generated when NBDA is obtained by the catalytic hydrogenation of DCN due to existence of such an impurity. Then, the amount of a phosphate present in a phosphite as an impurity is controlled, whereby the amount of the phenol generated from the phosphate is reduced and NBDA with less time-dependent coloring is obtained. Thus, the present invention has been completed.

That is, the present invention is specified by the following matters:

[1] a process for producing dicyanonorbornane characterized by causing hydrogen cyanide to undergo addition reaction with cyanonorbornene (bicyclo[2.2.1]-5-heptene-2-carbonitrile) in the presence of a zerovalent nickel complex catalyst which is produced by using a phosphite represented by P(x)(y)(z) (wherein P is a phosphorus atom, and x, y and z are each OR, where R represents an aryl group having not more than 18 carbon atoms) as a ligand to reduce a nickel halide with at least one metal selected among zinc, cadmium, beryllium, aluminum, iron and cobalt, wherein the phosphite is one which has a phosphate content of 1.0 weight % or lower based on the whole phosphite;

[2] the production process as set forth in [1], in which R is a phenyl group;

[3] the production process as set forth in [1] or [2], in which at least one metal is zinc;

[4] a zerovalent nickel complex catalyst produced by using a phosphite represented by P(x)(y)(z) (wherein P is a phosphorus atom, and x, y and z are each OR, where R represents an aryl group having not more than 18 carbon atoms) as a ligand to reduce a nickel halide with at least one metal selected among zinc, cadmium, beryllium, aluminum, iron and cobalt, wherein the phosphite is one which has a phosphate content of 1.0 weight % or lower based on the whole phosphite;

[5] the zerovalent nickel complex catalyst as set forth in [4], wherein R is a phenyl group;

[6] the zerovalent nickel complex catalyst as set forth in [4] or [5], wherein at least one metal is zinc;

[7] dicyanonorbornane obtained by the production process as set forth in any one of [1] to [3]; and

[8] a process for producing 2,5(6)-bis aminomethyl-bicyclo[2,2,1]heptane in which dicyanonorbornane as set forth in [7] is subjected to the catalytic hydrogenation. There has been proposed that very difficult problems in the prior art are overcome.

In the present invention, a phosphite used is one which has a phosphate content of 1.0 weight % or lower based on the whole phosphite, whereby it is possible to suppress the amount of phenol generated when NBDA is obtained by the catalytic hydrogenation of the obtained DCN. The present invention is to stably provide NBDA with reduced time-dependent coloring without a troublesome operation of adding caustic soda at the time of distilling NBDA.

BEST MODE FOR CARRYING OUT THE INVENTION

The present invention relates to a process for producing dicyanonorbornane. More particularly, the invention relates to a process for producing dicyanonorbornane (hereinafter referred to as DCN) by causing hydrogen cyanide to undergo reaction with cyanonorbornene (bicyclo[2.2.1]-5-heptene-2-carbonitrile, hereinafter referred to as CNN) using a zerovalent nickel complex catalyst and a Lewis acid cocatalyst.

In the first embodiment of the present invention, a phosphite as described below is used when a zerovalent nickel complex catalyst is produced by a phosphite represented by P(x)(y)(z) (wherein P is a phosphorus atom and x, y and z are each OR, where R each independently represents an aryl group having not more than 18 carbon atoms) as a ligand to reduce a nickel halide with at least one metal selected among zinc, cadmium, beryllium, aluminum, iron and cobalt. Namely, a phosphite used is one which has a phosphate content of 1.0 weight % or lower based on the whole phosphite. The present invention relates to a process for producing dicyanonorbornane characterized by causing hydrogen cyanide to undergo reaction with cyanonorbornene (bicyclo[2.2.1]-5-heptene-2-carbonitrile) in the presence of the zerovalent nickel complex catalyst which is produced by using such a phosphite.

The zerovalent nickel complex catalyst and the Lewis acid cocatalyst are synthesized according to the following chemical reaction formula (1),

$$NiX_2 + M + 4L \rightarrow NiL_4 + MX_2 \quad (1)$$

wherein, in the formula (1), X is a halogen atom; M is at least one metal selected among zinc, cadmium, beryllium, aluminum, iron and cobalt; and L is a ligand P(x)(y)(z) of a phosphite. In the ligand P(x)(y)(z), P is a phosphorus atom, x, y and z are each OR, and R is an aryl group having not more than 18 carbon atoms. R is preferably a phenyl group.

Therefore, the above $NiX_2$ is a nickel halide and the above $NiL_4$ is a zerovalent nickel complex catalyst. The above $MX_2$ is a metal halide generated by the result of the reduction reaction, but there is an effect of extending the life of a catalyst as a Lewis acid cocatalyst, and either of them can be used at the same time without isolating and purifying.

Incidentally, when M is aluminum, the catalysts are synthesized according to the following chemical reaction formula (2),

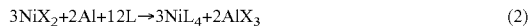

$$3NiX_2 + 2Al + 12L \rightarrow 3NiL_4 + 2AlX_3 \quad (2)$$

Preferred examples of the Lewis acid cocatalyst include zinc chloride, cadmium chloride, chromium chloride and aluminum trichloride. Particularly preferably used is zinc chloride.

In the present invention, according to the above chemical reaction formula (1) or (2), a nickel halide is reduced. As a reducing agent, at least one metal selected among zinc, cadmium, beryllium, aluminum, iron and cobalt is used. The reducing agent is most preferably zinc. As a result of the reduction of the nickel halide, the zerovalent nickel complex catalyst and the Lewis acid cocatalyst are synthesized.

The amount of the above reducing agent is preferably an excess equivalent than that of the nickel halide from the viewpoint of enhancing the yield of the zerovalent nickel catalyst. Specifically, the molar ratio of the reducing agent to the nickel halide is preferably from 1 to 6.

In the present invention, the reaction for synthesizing the zerovalent nickel complex catalyst and the Lewis acid cocatalyst is carried out in the presence of water. To add water, water per se may be added to the reaction system. However, when the nickel halide is a hydrate, its water of hydration can also be used. The amount of water needed for the synthesis of the catalyst is preferably from 0.5 to 40 mole, more preferably from 0.8 to 30 mole and further preferably from 1 to 20 mole, based on 1 mole of the nickel atom contained in the nickel halide. When the amount of water is within the above range, high catalytic synthesis yield is achieved. In particular, when the amount of water is not more than 40 mole, high catalytic synthesis yield is achieved and at the same time high catalytic stability is achieved in causing hydrogen cyanide to undergo reaction with CNN.

Herein, preferred examples of the nickel halide include, for example, nickel chloride, nickel bromide and nickel iodide, and the nickel halide may be an anhydrous salt or a hydrate thereof. Most preferably used in view of handling is a hydrate of nickel chloride.

In the present invention, preferred examples of the phosphite represented by P(x)(y)(z) as a ligand include triaryl phosphites such as triphenyl phosphite, tri(m- or p-chlorophenyl)phosphite, tri(m- or p-methoxyphenyl)phosphite, tri(m- or p-cresyl)phosphite, tri(m- or p-nonylphenyl)phosphite or the like, and a mixture thereof. More preferred examples include triaryl phosphites, and further preferred examples include triphenyl phosphite, tri(m- or p-cresyl) phosphite and tri(m- or p-nonylphenyl)phosphite.

The content of the phosphate that is an impurity contained in the phosphite of the present invention is greatly different depending on various circumstances so that an allowance at the step just before its use needs to be clarified. The content of phosphate that is an impurity is different, for example, depending on storage or transfer status during production and after the production of phosphite, the difference in the production maker or production lot, further handling status right before the use and the like. An allowance of the impurity is determined from the viewpoint of suppressing an increase of phenol which is present in NBDA as an impurity when NBDA with less time-dependent coloring is obtained by carrying out the catalytic hydrogenation of the obtained DCN. Specifically, the content of phosphate present in a raw material phosphite is not more than 1.0 weight % based on the total weight of phosphite. Such a phosphite is selected and used. The content of a phosphate is more preferably not more than 0.7 weight % and further preferably not more than 0.4 weight % for bringing about result. As a purifying method of the phosphite cited herein, there can be cited 1) a method involving heating and removing a solvent, a low boiling substance or the like under a reduced pressure, 2) purifying by distillation and 3) purifying by recrystallization.

The amount of the phosphite as a ligand of the present invention may be chemical equivalent, that is, about 4 mole based on the nickel halide. Within the above range, the yield of the zerovalent nickel complex is less affected. However, it is more preferably not less than 5 mole from the viewpoint of enhancing activities at the time of hydrogen cyanide reaction and life, but further preferably from 6 to 36 mole and further more preferably from 8 to 20 mole. The reaction may not be hindered even if the amount exceeds 36 mole, but it is not always economical in consideration of post treatment of the hydrogen cyanide reaction solution and loss at the time of purifying and ligand recovery.

In the synthesis of the zerovalent nickel complex catalyst, the aforementioned ligand can also play a role of a solvent. However, in addition thereto, a new solvent may be used as long as it does not hinder the reaction. Examples of the solvent to be used include aromatic hydrocarbon compounds such as benzene, toluene, xylene, ethylbenzene and the like; nitrile solvents such as acetonitrile, benzonitrile, CNN and the like; ether solvents such as dioxane, o-methoxybenzene, tetrahydrofuran, dimethoxyethane, diethoxyethane and the like; aromatic halogenated hydrocarbon solvents such as o-dichlorobenzene, p-dichlorobenzene and the like; and analogous compounds.

As the condition for the synthesis of the zerovalent nickel complex catalyst, the nickel content in the nickel halide is not particularly restricted, but it is preferably from 0.1 to 2% based on the total charge weight. The temperature is usually from 0 to 150 degrees centigrade and preferably from 40 to 100 degrees centigrade in consideration of the reaction yield, reaction time and decomposition of the catalyst. The reaction time is more preferably within 2 hours when the industrial efficiency is emphasized.

Next, a method for producing DCN by causing hydrogen cyanide to undergo reaction with CNN will be described.

In the present invention, with respect to the charge ratio of the zerovalent nickel complex catalyst synthesis solution and the raw material CNN, the molar ratio of CNN to the zerovalent nickel catalyst synthesis solution is preferably from 20 to 5,000 and more preferably from 100 to 2,000 in consideration of volume efficiency or slurry property and purification load in the post-step.

As CNN used as a raw material in the present invention, there can be usually used those industrially produced from the Diels-Alder reaction of acrylonitrile with cyclopentadiene or dicyclopentadiene.

On the other hand, as the hydrogen cyanide used in the present invention, there can be used those industrially produced by taking out a by-product of acrylonitrile in an ammoxidation method using methane, ammonia and air as raw materials, or an ammoxidation method using propylene, ammonia and air.

The amount of the hydrogen cyanide can be any optional molar amount as long as it is not less than 1 mole based on 1 mole of CNN, but it is usually 1 mole. Furthermore, the reaction temperature of hydrogen cyanide of CNN is preferably from −20 to 200 degrees centigrade, more preferably from 0 to 130 degrees centigrade and further preferably from 20 to 100 degrees centigrade. The reaction pressure may be either atmospheric pressure or applied pressure, but the reaction is usually carried out in atmospheric pressure because an increase in pressure does not cause the improvement in a remarkable effect on reaction acceleration or selectivity.

As the reaction type of causing hydrogen cyanide to reaction with CNN in the present invention, a batch reaction is usually adopted, but there is also adopted a continuous reaction such that CNN, hydrogen cyanide, a zerovalent nickel complex catalyst synthesis solution or as needed a solvent and the like are continuously supplied.

DCN produced according to the present invention is obtained, for example, as a mixture containing 2,5-dicyanonorbornane (bicyclo[2.2.1]heptane-2,5-dicarbonitrile) and 2,6-dicyanonorbornane (bicyclo[2.2.1]heptane-2,6-dicarbonitrile) as main ingredients.

Furthermore, a process for producing 2,5(6)-bis aminomethyl-bicyclo[2,2,1]heptane (hereinafter referred to as NBDA) by the catalytic hydrogenation of DCN will be described.

As a method for producing NBDA, the following methods can be cited. Firstly, DCN, 25 weight % ammonia water (30 mole % based on DCN) and a Raney nickel catalyst (about 1 weight % based on DCN) were introduced for carrying out the catalytic hydrogenation under conditions of hydrogen pressure of about 3.5 MPa and a temperature of 120 degrees centigrade. Thereafter, a catalyst is removed, then ammonia water and toluene are distilled off.

Most of phenol contained in NBDA of the present invention is derived from acid decomposition of a zerovalent nickel complex catalyst and a cocatalyst used in the production of a raw material DCN or hydrolysis. The content of phenol in NBDA with less time-dependent coloring is, for example, not more than 0.05 weight % and preferably not more than 0.02 weight %.

The content of phenol in NBDA is a value obtained from the gas chromatography analysis. Specifically, phenol in NBDA is measured by an absolute calibration curve method or the like in the gas chromatography analysis.

As a method for reducing the content of phenol in NBDA, a means involving adding a strong base for carrying out distillation or the like is cited in Patent Document 5. However, in the present invention, as described above, the zerovalent nickel complex catalyst is produced by using a phosphite, wherein the phosphite is one which has a phosphate content of not more than a prescribed amount. As a result, as in the past, even without an operation for reducing the content of phenol in DCN or NBDA, NBDA with less time-dependent coloring is stably obtained.

EXAMPLES

The effect of the present invention is now illustrated in detail below with reference to Examples. However, the present invention is not restricted to these Examples. The amount of a phosphite of triphenyl phosphite (hereinafter referred to as TPP) used herein and a phosphate of triphenyl phosphate in DCN, and the amount of phenol in NBDA were analyzed by gas chromatography.

In a method of judging time-dependent coloring, the color tone of NBDA which was stored for a prescribed period of time was represented by the color tone APHA method according to Clause 5.1 of JIS K1556. Specifically, using a standard solution prepared by dissolving a reagent of platinum and cobalt, it was obtained by comparing to a standard liquid diluent with darkness equivalent to the color of the sample, and its degree was taken as a measured value of APHA. The color tone was good as this degree is smaller. NBDA with less time-dependent coloring refers to APHA of not more than 10.

Example 1

Into a 50-ml glass round bottom flask equipped with a stirrer, a thermometer, a nitrogen inlet tube and a condenser were introduced 1.07 g (4.5 mmol) of nickel chloride hexahydrate, 0.60 g (9.2 mmol) of zinc, 8.90 g (28.7 mmol) of TPP containing 0.2 weight % of triphenyl phosphate purified by a known method and 26.5 g (22.2 mmol) of CNN, and the replacement with nitrogen was surely carried out for the gas phase to obtain a tetrakis(triphenyl phosphite) nickel catalyst. Next, into a 1-L glass flat bottom separable flask equipped with a stirrer, a thermometer, a nitrogen inlet tube, a hydrogen cyanide inlet tube and a condenser were introduced 307.0 g (2.58 mol) of CNN, 90.0 g of toluene and the catalyst synthesis solution obtained as above, and the replacement with nitrogen was fully carried out for the gas phase at room temperature and then the temperature was elevated to 60 degrees centigrade. Then, 69.13 g (2.66 mol) of liquid hydrogen cyanide was supplied over 3.5 hours and hydrogen cyanide reaction was carried out to obtain 480.7 g of a coarse DCN.

Nitrogen gas was bubbled in 480.7 g of the resulting coarse DCN at a flow rate of 500 ml/min for 1 hour for degassing, and then insoluble substances were filtered off. To this filtrate was added 1.9 g of 40% sulfuric acid, and the resulting solution was heated at 60 degrees centigrade for 3 hours for carrying out acid decomposition of the catalyst. 5.5 g of 25 weight % sodium hydroxide was further added thereto and the mixture was heated at 40 degrees centigrade for 2 hours and neutralized, and then 449.0 g of toluene was added for extracting DCN to obtain a DCN toluene solution. Then, toluene was removed to obtain 447.6 g of 85 weight % DCN. The resulting DCN was analyzed and as a result, triphenyl phosphate was not contained therein.

Next, into a 500-ml autoclave were introduced 287.8 g of DCN obtained above, 32.6 g of 25% ammonia water and 7.9 g of a Raney cobalt catalyst, and the catalytic hydrogenation reaction was carried out at 120 degrees centigrade at hydrogen pressure of 3.5 MPa for 430 minutes. The resulting solution was cooled to room temperature and filtered to remove the Raney cobalt catalyst, and then 0.5 g of 32 weight % caustic soda was added to the filtrate for removing ammonia and toluene contained in DCN at 75 degrees centigrade at 2.6 KPa. Subsequently, the resulting residue was distilled under conditions of 0.1 MPa and a temperature in the flask of 150 to 160 degrees centigrade to obtain 204 g of NBDA. Phenol was analyzed and as a result, NBDA did not contain phenol. Furthermore, the obtained NBDA was sealed with nitrogen and then tightly closed up. The resultant was stored in a light-shielded vessel at room temperature (25 to 35 degrees centigrade) for 1 month and then time-dependent coloring was confirmed and as a result, no time-dependent coloring was found as APHA was not more than 10. The test results are shown in Table 1.

Example 2

The test was conducted in the same manner as in Example 1 using TPP containing 0.6 weight % of triphenyl phosphate. Said TPP was purified by a known method. The resulting DCN was analyzed and as a result, 0.08 weight % of triphenyl phosphate was contained therein. NBDA obtained by using this DCN contained 0.04 weight % of phenol. However, it was stored in a light-shielded vessel at room temperature (25 to 35 degrees centigrade) for 1 month and then time-dependent coloring was confirmed and as a result, no time-dependent coloring was found as APHA was not more than 10. The test results are shown in Table 1.

Comparative Example 1

The test was conducted in the same manner as in Example 1 using TPP containing 1.1 weight % of triphenyl phosphate. The resulting DCN was analyzed and as a result, 0.25 weight % of triphenyl phosphate was contained therein. NBDA obtained by using this DCN contained 0.20 weight % of phenol. It was stored in a light-shielded vessel at room temperature (25 to 35 degrees centigrade) for 1 month and then time-dependent coloring was confirmed and as a result, time-dependent coloring was confirmed as APHA was 30. The test results are shown in Table 1.

TABLE 1

| | Amount of triphenyl phosphate in triphenyl phosphite (weight %) | Amount of triphenyl phosphate in DCN (weight %) | Amount of phenol in NBDA (weight %) | Time-dependent coloring of NBDA |
|---|---|---|---|---|
| Example 1 | 0.2 | 0 | 0 | No |
| Example 2 | 0.6 | 0.08 | 0.04 | No |
| Comparative Example 1 | 1.1 | 0.25 | 0.20 | Yes |

According to the present invention, it is possible to stably provide NBDA with no time-dependent coloring.

The invention claimed is:

1. A process for producing dicyanonorbornane, comprising:
    a step of purifying a phosphite represented by P(x)(y)(z) (wherein P is a phosphorus atom, and x, y and z are each OR, where R represents an aryl group having not more than 18 carbon atoms) by distillation to reduce a phosphate content to 1.0 weight % or lower based on the whole phosphite, and
    a step of causing hydrogen cyanide to undergo addition reaction with cyanonorbornene (bicyclo[2.2.1]-5-heptene-2-carbonitrile) in the presence of a zerovalent nickel complex catalyst which is produced by using the phosphite as a ligand to reduce a nickel halide with at least one metal selected among zinc, cadmium, beryllium, aluminum, iron and cobalt, wherein the phosphite is one which has the phosphate content of 1.0 weight % or lower based on the whole phosphite.

2. The process for producing dicyanonorbornane as set forth in claim 1, in which said R is a phenyl group.

3. The process for producing dicyanonorbornane as set forth in claim 1, in which said at least one metal is zinc.

4. The process for producing dicyanonorbornane as set forth in claim 2, in which said at least one metal is zinc.

* * * * *